United States Patent
McCutcheon et al.

(10) Patent No.: US 8,380,271 B2
(45) Date of Patent: Feb. 19, 2013

(54) SYSTEM AND METHOD FOR GENERATING CUSTOMIZABLE AUDIBLE BEEP TONES AND ALARMS

(75) Inventors: Ian McCutcheon, Pleasanton, CA (US); Jayesh Shah, Pleasanton, CA (US)

(73) Assignee: Covidien LP, Mansfield, MA (US)

( * ) Notice: Subject to any disclaimer, the term of this patent is extended or adjusted under 35 U.S.C. 154(b) by 1617 days.

(21) Appl. No.: 11/453,693

(22) Filed: Jun. 15, 2006

(65) Prior Publication Data
US 2007/0293745 A1 Dec. 20, 2007

(51) Int. Cl.
*A61B 5/1455* (2006.01)
(52) U.S. Cl. .......... 600/323; 600/310
(58) Field of Classification Search ........... 600/309–344
See application file for complete search history.

(56) References Cited

U.S. PATENT DOCUMENTS

| | | | |
|---|---|---|---|
| 3,638,640 A | 2/1972 | Shaw | |
| 4,653,498 A | 3/1987 | New et al. | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A * | 3/1993 | Polson et al. | 600/330 |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |

(Continued)

FOREIGN PATENT DOCUMENTS

| | | |
|---|---|---|
| EP | 0615723 | 9/1994 |
| EP | 0630203 | 12/1994 |

(Continued)

OTHER PUBLICATIONS

Philips, Patient Monitoring, FAST-SpO$_2$ Pulse oximetry, http://www.medical.philips.com/main/products/patient_monitoring/products/fast_spo2ind . . . , Jun. 15, 2006, 3 pages.

(Continued)

*Primary Examiner* — Eric Winakur
*Assistant Examiner* — Marjan Fardanesh

(57) ABSTRACT

A pulse oximetry system adapted to obtain physiological data. The pulse oximetry system is adapted to store one or more digital audio files on one or more memory media in communication with a patient monitoring system. The pulse oximetry system is adapted to process the one or more digital audio files and to generate an audio signal in response to the physiological data.

20 Claims, 5 Drawing Sheets

U.S. PATENT DOCUMENTS

| | | | |
|---|---|---|---|
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,730,140 A * | 3/1998 | Fitch | 600/514 |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | Delonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,398,727 B1 | 6/2002 | Bui et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,449,501 B1 | 9/2002 | Reuss | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,542,764 B1 * | 4/2003 | Al-Ali et al. | 600/323 |
| 6,544,193 B2 | 4/2003 | Abreu | |
| 6,546,267 B1 | 4/2003 | Sugiura et al. | |
| 6,549,795 B1 | 4/2003 | Chance | |
| 6,579,242 B2 | 6/2003 | Bui et al. | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Pishney et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,771,994 B2 | 8/2004 | Kiani et al. | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,830,549 B2 | 12/2004 | Bui et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,865 B1 | 2/2006 | Cohen et al. | |
| 7,024,233 B2 | 4/2006 | Ali et al. | |
| 7,024,235 B2 | 4/2006 | Melker et al. | |
| 7,027,849 B2 | 4/2006 | Al-Ali | |
| 7,070,570 B2 * | 7/2006 | Sanderson et al. | 600/532 |
| 7,138,575 B2 * | 11/2006 | Childs et al. | 84/615 |
| 7,149,570 B2 * | 12/2006 | Ellscheid et al. | 600/519 |
| 7,231,229 B1 * | 6/2007 | Hawkins et al. | 455/564 |
| 7,511,213 B2 * | 3/2009 | Childs et al. | 84/615 |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0068164 A1 | 4/2004 | Diab et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0133087 A1 | 7/2004 | Ali et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0193026 A1 | 9/2004 | Scharf | |
| 2004/0230106 A1 | 11/2004 | Schmitt et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0251214 A1 | 11/2005 | Parascandola et al. | |
| 2005/0267346 A1 | 12/2005 | Faber et al. | |

| | | | |
|---|---|---|---|
| 2005/0283059 | A1 | 12/2005 | Iyer et al. |
| 2006/0009688 | A1 | 1/2006 | Lamego et al. |
| 2006/0015021 | A1 | 1/2006 | Cheng |
| 2006/0020181 | A1 | 1/2006 | Schmitt |
| 2006/0030763 | A1 | 2/2006 | Mannheimer et al. |
| 2006/0052680 | A1 | 3/2006 | Diab |
| 2006/0058683 | A1 | 3/2006 | Chance |
| 2006/0058691 | A1 | 3/2006 | Kiani |
| 2006/0064024 | A1 | 3/2006 | Schnall |
| 2006/0195025 | A1 | 8/2006 | Ali et al. |
| 2006/0195028 | A1 | 8/2006 | Hannula et al. |
| 2006/0224058 | A1 | 10/2006 | Mannheimer |
| 2006/0226992 | A1 | 10/2006 | Al-Ali et al. |
| 2006/0238358 | A1 | 10/2006 | Al-Ali et al. |
| 2006/0247501 | A1 | 11/2006 | Ali |
| 2006/0258921 | A1 | 11/2006 | Addison et al. |
| 2008/0300474 | A1 | 12/2008 | Benni et al. |

FOREIGN PATENT DOCUMENTS

| | | |
|---|---|---|
| JP | 63275325 | 11/1988 |
| JP | 2237544 | 9/1990 |
| JP | 8256996 | 10/1996 |
| JP | 2005034472 | 2/2005 |
| WO | WO9639927 | 12/1996 |
| WO | WO0021438 | 4/2000 |
| WO | WO0140776 | 6/2001 |
| WO | WO0176461 | 10/2001 |
| WO | WO0176471 | 10/2001 |
| WO | 01/91635 A | 12/2001 |
| WO | WO03039326 | 5/2003 |
| WO | 2004017831 A | 3/2004 |
| WO | WO 2007017777 | 2/2007 |

OTHER PUBLICATIONS

Scotty, Integrated Digital Stethoscope, wwwscottygroup.com, Jun. 15, 2006, 2 pages.

Sweet Beats.net, Fetal Monitor—Standard, http://www.sweetbeats.net/fetal-monitor.php, Jun. 15, 2006, 2 pages.

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2230-2332.

East, Christine E., et al.; "Fetal Oxygen Saturation and Uterine Contractions During Labor," *American Journal of Perinatology*, vol. 15, No. 6, pp. 345-349 (Jun. 1998).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Yoon, Gilwon, et al.; "Multiple diagnosis based on Photoplethysmography: hematocrit, SpO2, pulse and respiration," *Optics in Health Care and Biomedical optics: Diagnostics and Treatment; Proceedings of the SPIE*, vol. 4916; pp. 185-188 (2002).

Johansson, A.; "Neural network for photoplethysmographic respiratory rate monitoring," *Medical & Biological Engineering & Computing*, vol. 41, pp. 242-248 (2003).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

* cited by examiner

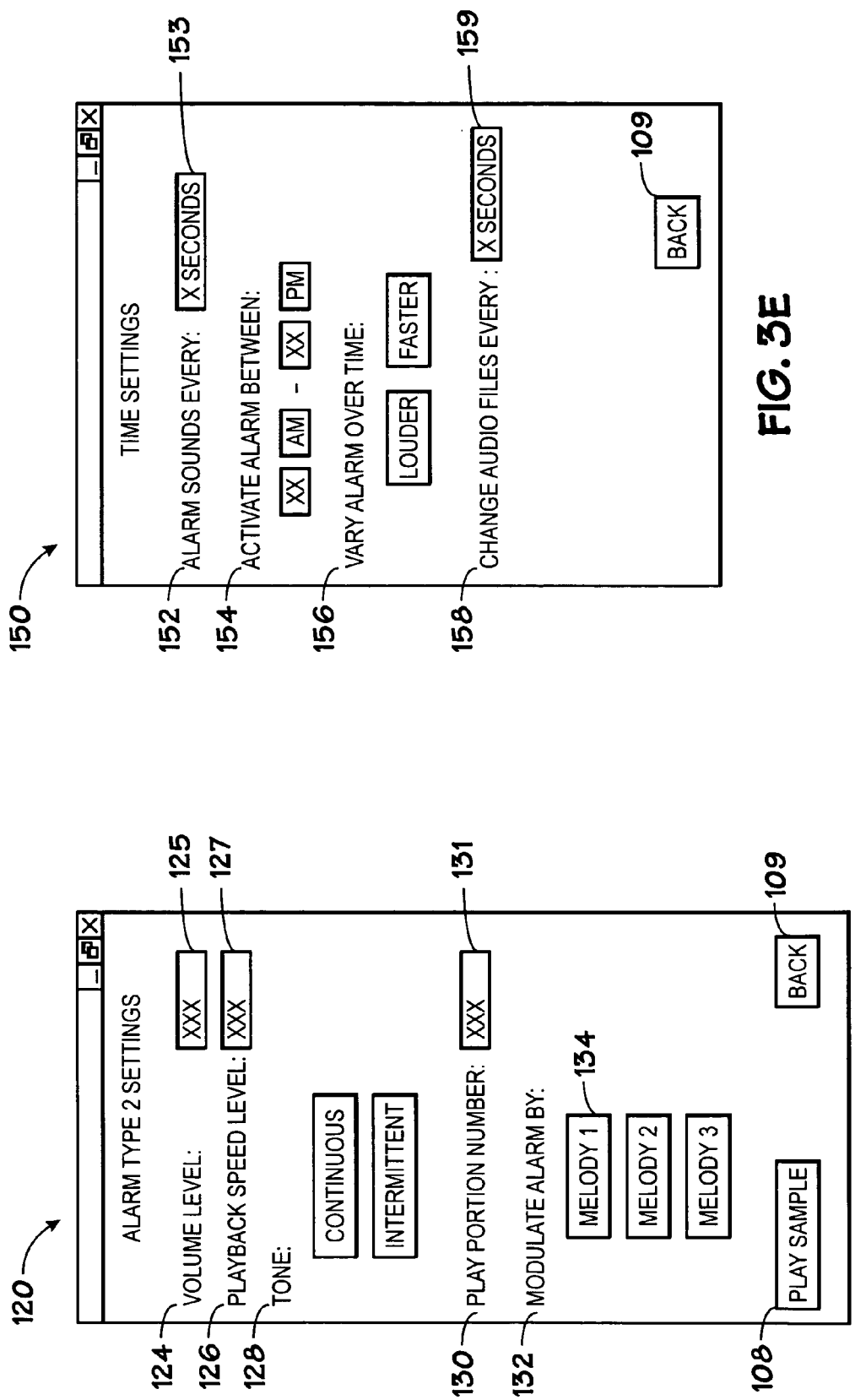

SYSTEM AND METHOD FOR GENERATING CUSTOMIZABLE AUDIBLE BEEP TONES AND ALARMS

BACKGROUND OF THE INVENTION

1. Field of the Invention

The present invention relates generally to pulse oximetry, and more particularly to tones and alarms generated by pulse oximetry systems.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation ($SpO_2$) of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically senses the absorption and/or scattering of the transmitted light in such tissue. Data of light absorbance and/or scatter in a patient's tissue is processed by the pulse oximetry system to derive meaningful and conveyable physiological data of the patient for use by clinicians. Accordingly, pulse oximeters typically employ means to convey a patient's physiological parameters that are monitored by the pulse oximetry system. Correspondingly, changes in status of such parameters may invoke an appropriate action by a clinician to address such changes. As such, pulse oximetry systems normally employ audible alarms or beep tones, possibly comprising various frequencies, pitches, and/or volume amplitudes to convey physiologically monitored information, changes in such information or the absence of change in such information. Furthermore, in a clinical setting, such as an operating room, a patient may be monitored for numerous physiological parameters in addition to those associated with pulse oximetry. Hence, monitoring additional parameters may encompass additional audible systems, each having its own set of beeps and alarms. In such a setting, there exists a potential for confusion due to the number of audible monitoring tones and their potential similarity.

Furthermore, prolonged usage of specific monitoring equipment having distinctive alarms and beep tones may, over time, condition the clinician to respond to specific sounds generated by the monitoring system. Being conditioned to specific alarms which correspond to particular physiological parameters, a clinician can respond directly to a patient's needs without having to first physically access the monitoring system. Consequently, replacement of monitoring equipment having different alarm types may necessitate a clinician to recondition his/hers reaction to correspond to the new alarm and/or tone. Therefore, it may be time consuming and inconvenient for a clinician to get adapted to new alarm types in instances where monitoring equipment is replaced. Further, this may lead to clinician error in misinterpreting alarms and/or tones, potentially causing the clinician to improperly respond to a medical condition.

BRIEF DESCRIPTION OF THE DRAWINGS

Advantages of the invention may become apparent upon reading the following detailed description and upon reference to the drawings in which:

FIGS. 3A-3F illustrate user configurable audio file settings, in accordance with aspects of one embodiment of the present technique.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The object of the present technique is to provide a system and method for generating customizable beep tones and alarms in pulse oximetry. Thus, for example, in order to distinguish one pulse oximeter from another a clinician can configure one or more pulse oximeters such that the clinician can distinguish between the beeps and alarms emitted by each oximeter. Additionally, pulse oximeters with customizable alarms and beep tones may be configurable to generate alarms and beep tones associated with other pulse oximeter types and models. Accordingly, such flexibility is advantageous, especially when one pulses oximetery model is replaced by another. Hence, a clinician can configure the monitoring equipment's alarms and beep tones to be similar or identical to previously used equipment.

Figure 1:
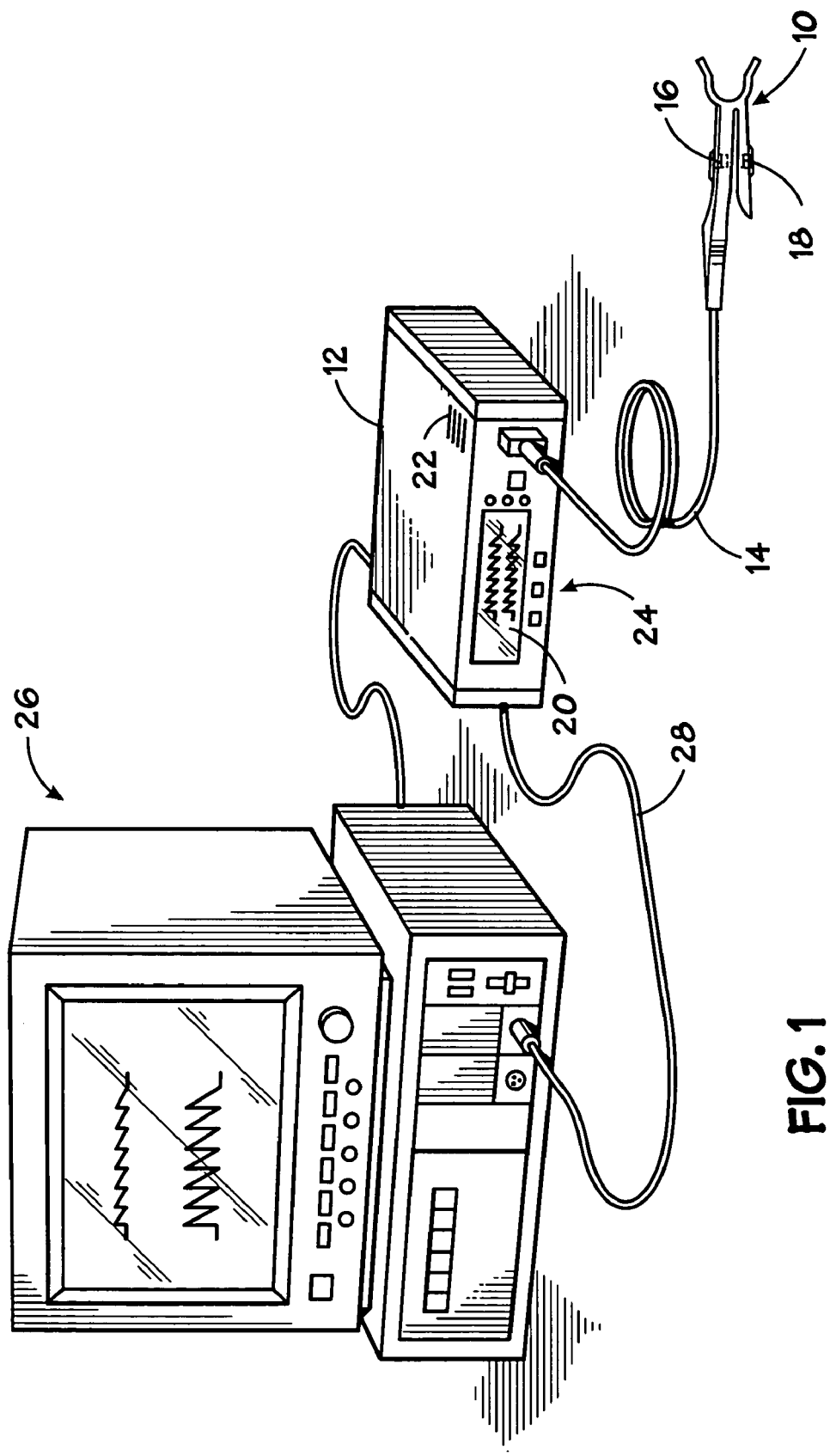
FIG. 1 illustrates a patient monitoring system coupled to a single or a multi-parameter patient monitor and a sensor, in accordance with aspects of one embodiment of the present technique.

Referring now to FIG. 1, a patient monitoring system includes a sensor 10 which according to the present invention may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

The sensor 10, in the example depicted in FIG. 1, includes an emitter 16 and a detector 18 which may be of any suitable type. For example, the emitter 16 may be one or more light emitting diodes adapted to transmit one or more wavelengths of light, such as in the red to infrared range, and the detector 18 may be a photodetector, such as a silicon photodiode package, selected to receive light in the range emitted from the emitter 16. In the depicted embodiment, the sensor 10 is coupled to a cable 14 that is responsible for transmitting electrical and/or optical signals to and from the emitter 16 and/or detector 18 of the sensor 10. The cable 14 may be permanently coupled to the sensor 10, or it may be removably coupled to the sensor 10—the latter alternative being more useful and cost efficient in situations where the sensor 10 is disposable.

The patient monitor 12 comprises display 20, a speaker 22 (such as a high-fidelity speaker), and a keypad 24. These components are adapted to configure and play digital and/or analog audio files stored within or accessed by the patient monitor 12. The patient monitor 12 may further be connected to a computer 26, via cable 28. The computer 26 may be used to couple the patient monitor 12 to a network, such as internet.

Figure 2:
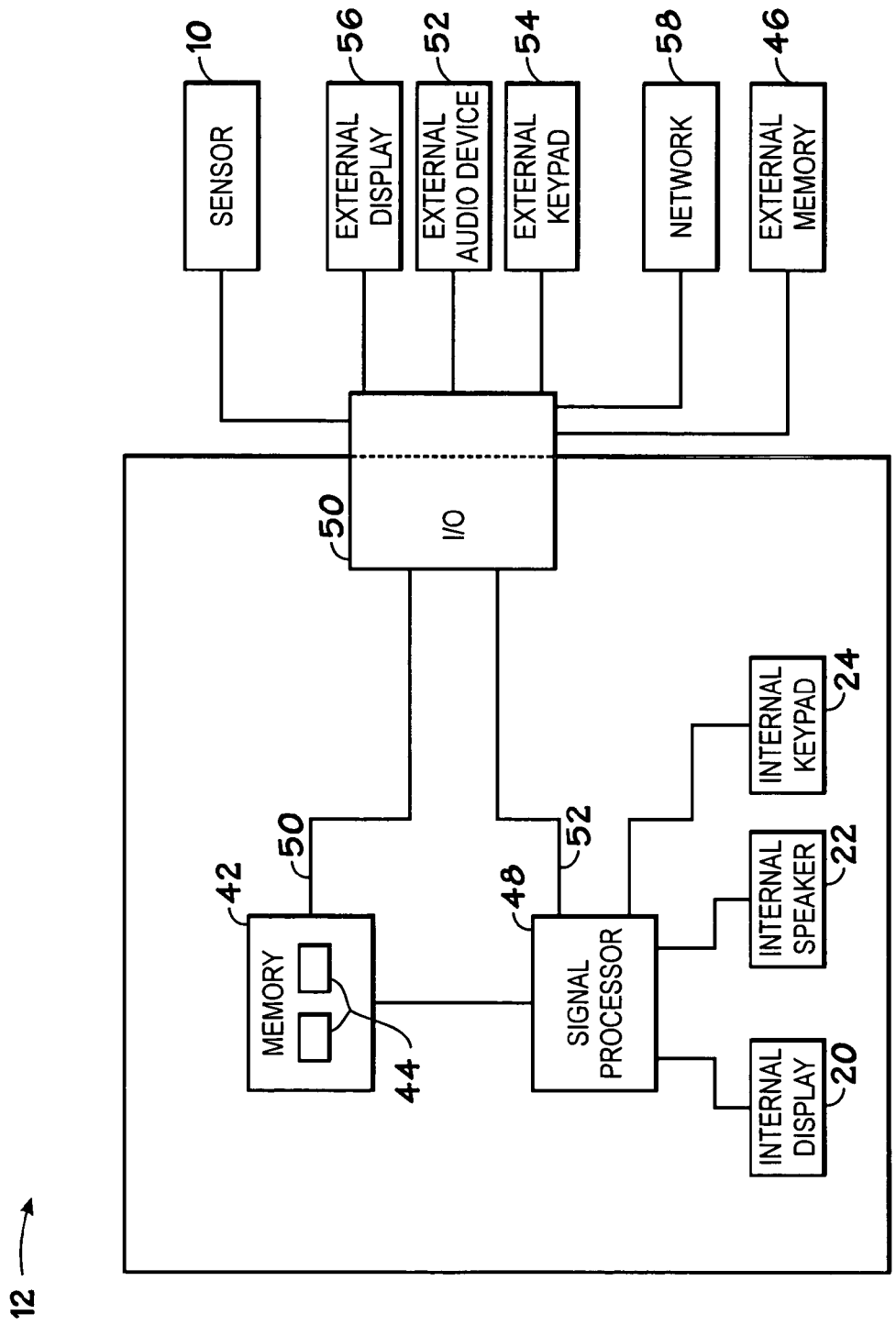
FIG. 2 is a block diagram illustrating the hardware component of the single or the multi-parameter patient monitor, in accordance with aspects of one embodiment of the present technique.

Referring now to FIG. 2, a block diagram represents an exemplary embodiment of the monitor 12 having internal and external hardware components. The components depicted by the diagram are adapted to facilitate use of digital and analog audio files in conjunction with pulse oximetry. In one embodiment, memory 42 (such as magnetic, solid-state, and/or optical memory components) is adapted to store digital audio files 44 in respective memory regions. As will be appreciated to those of ordinary skill in the art, audio files may also be stored in external memory devices 46, such as a compact flash card or a USB memory stick or other suitable connectable memory medium, via a suitable external memory interface. Accordingly, the digital audio files can be used to generate various audible beeps and alarms in accordance with one or more physiological parameters monitored by the patient monitor 12.

Digital audio files 44 stored in memory 42 or memory device 46 may include file formats such as ".wav", ".mp3", ".aif", ".aiff", ".au", ".wma", ".qt", ".ra", ".ram", ".mp4", AAC (AIFF, AIFC), and other formats by which audio is saved digitally. The patient monitor 12 may further save or play audio files generated by source code executed by a signal processor. In one exemplary embodiment, the digital audio files may be stored in memory 42 and accessed by a user during patient monitoring. The digital audio files may further be pre-installed and stored during manufacture and assembly of the patient monitor or, alternatively, they can be downloaded from a computer, a server, and/or a network. Similarly, the digital audio files may be downloaded or accessed from a consumer electronic device, such as a portable music player, cellular telephone, etc, via a suitable interface, such as a USB and/or a serial interface of the patient monitor 12. Similarly, a suitable interface can be implemented as a wireless communication device (not shown) coupled to the patient monitor 12 and the computer 26 of FIG. 1, such that the digital audio files may be downloaded wirelessly. In one embodiment, the patient monitor 12 may have the capability to digitally record and store audible signals for retrieval and playing upon demand.

Internal memory 42 and/or external memory 46 are coupled to a signal processor 48. The signal processor 48 is configured to process the digital audio files by converting these files to signals which may be audiblized when played on an attached speaker. Thus, the signal processor 48 may further comprise components, such as analog to digital converters and amplifiers adapted to generate the audio signals and may be configured to execute corresponding software routines. The software routines may include suitable algorithms adapted to output audio signals in accordance with the physiological data or changes thereof.

In one embodiment, the signal processor 48 is coupled to the internal speaker 22 (such as a high-fidelity speaker), the internal display 20, the internal keypad 24, and/or to an Input/Output (I/O) interface 50. The internal speaker 22 facilitates conversion of the signal generated by signal processor 48 into sound. The internal display 20 and the internal keypad 24 facilitate user configuration of alarms and beep tones generated by the digital audio files and associations of such settings with specific physiological events. In an exemplary embodiment, the display itself may include a touchable keypad for configuration of the patient monitor 12.

Further, the memory 42 and/or the signal processor 48 may be coupled to external devices via the I/O 50. For example, pulse oximetry data, such as oxygen saturation, is transferred via I/O 50 from the sensor 10 to the signal processor 48 for processing and/or to the memory 42 for storage. Accordingly, the signal processor 48 may generate audio signals which correspond to or otherwise relate to physiological information obtained by the sensor 10. The generated signals may be transmitted to the internal speaker 22 and/or to an external audio device 52 (such as a high-fidelity speaker, an ear piece etc.). In one exemplary embodiment, the external audio device 52 may comprise a back-up audible system, operable only in the event speaker 22 is not. In other exemplary embodiments, speakers 22 and 52 can be simultaneously operable or they can each be configured to sound different beeps and/or alarms.

Additionally, in one embodiment, an external keypad 54 and an external display 56 are connected via I/O ports 50. These devices may enable, for example, users to remotely configure the patient monitor 12. Furthermore, network connection 58 (such as an Internet connection) may be accomplished via a network port on the monitor 12 or via a network connection or an intermediate device, such as computer 26, connected via cable 28 (FIG. 1) to the I/O 50. Accordingly, audio files can be downloaded to the patient monitor 12, stored in memory 42 and/or processed by the signal processor 48 to generate customizable audible beep tones and/or alarms. It should be emphasized that, in some embodiments, the external devices 10, 46, 52, 54, 56 and other devices may wirelessly communicate with the patient monitor 12 via the I/O 50 or via a device specific interface.

In accordance with the present technique, a user, such as a clinician, can configure the patient monitor 12 to sound specific audible tones, saved as audio files as described above, corresponding to monitored states of physiological parameters. In an exemplary embodiment, a clinician may configure the patient monitor 12 via the display 20, 56, and via the keypad 24, 54. In accordance with the present technique, FIGS. 3A-3F illustrate exemplary screens for the configuration of settings related to generating beep tones and alarms using audio files, as discussed further below.

Figure 3C:
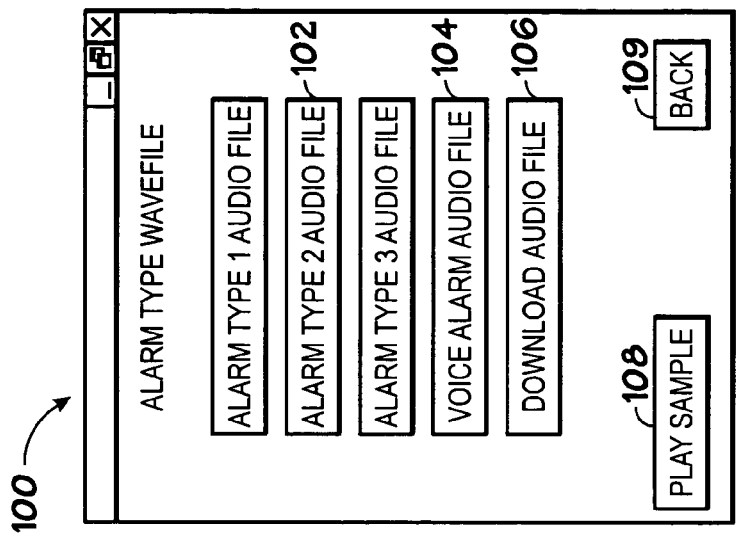
Figure 3B:
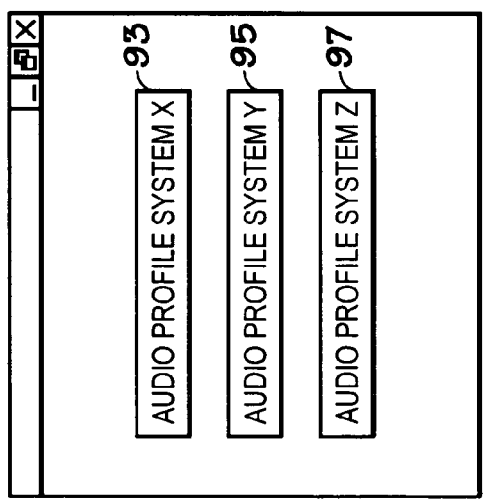
Figure 3A:
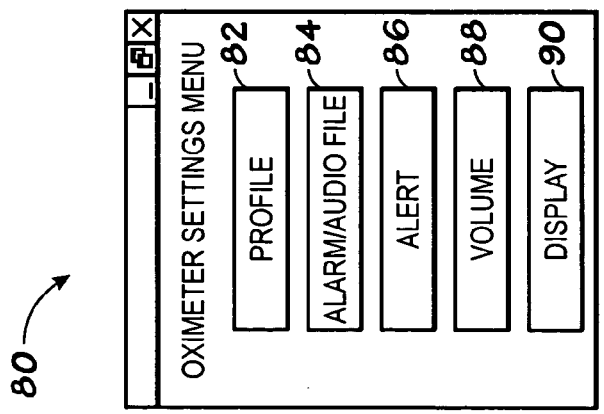

Referring to FIG. 3A, an embodiment including exemplary screen 80 labeled, OXIMETER SETTINGS MENU enables the user to initiate the configuration of the patient monitor 12. The screen 80 includes settings, such as PROFILE setting 82, ALARM/AUDIO FILE setting 84 and ALERT setting 86 discussed further below with reference to sequentially configuring alarm settings of the patient monitor 12. Screen 80 further comprises VOLUME setting 88, and DISPLAY setting 90. Accordingly, the VOLUME setting 88 sets a default volume level of the speaker 22 and/or the external audio device 54, while the DISPLAY setting 90 may control brightness, color, and textural features of the displays 20, 56.

The PROFILE setting 82 may configure the profile/theme of the patient monitor 12 to be distinct from or identical to a different model of patient monitor. For example, a clinician may desire to have the patient monitor 12 generate sounds that are identical to a patient monitor that is no longer in use, but whose alarm sounds are familiar to the clinician. Thereby, upon replacement or upgrading of a patient monitoring system, the clinician may not have to retrain his/hers reactions to new alarm sounds. Alternatively, it may be preferable for the clinician to distinguish the alarm sounds of one patient monitor from alarm sounds of other patient monitors operating in a vicinity of the patient monitor. In such a situation, the clinician may configure one or more monitors 12 to sound different from other nearby monitors.

Hence, in an exemplary embodiment, selection of profile option 82 leads the user to screen 91 (FIG. 3B) for further configuration of the patient monitor 12. Accordingly, the screen 91 lists respective options 93, 95, and 97 adapted to configure the profile/theme of the patient monitor 12 to be identical to particular patient monitoring systems. Thus, choosing option button 93 may, for example, configure the profile/theme of the patient monitoring 12 to that of a different model of a patient monitoring system. In so doing, the patient monitor 12 may emulate the other model's alarm and alert sounds, settings and characteristics. The options 95 and 97 may further configure the patient monitor 12 to emulate the alarm and alert settings of other patient monitoring systems. Advantageously, screen 91 enables a clinician to configure the patient monitor 12 as a different patient monitoring system with a stroke of a key.

Referring once again to screen 80, the ALARM/AUDIO FILE setting 84 controls features of alarms generated using audio files stored in respective memory regions of memory 42. These alarms may be activated when, for example, a patient's oxygen saturation level drops below a certain value, which prompts the clinician to react accordingly. The ALERT setting 86 controls beep tones generated using the stored audio files such that the beep tones may correspond to a continuous monitoring of physiological parameters and/or changes of such parameters thereof over time.

In this example, user selection of setting 84 ALARM/AUDIO FILE in screen 80 of FIG. 3A prompts the user to screen 100, depicted by an exemplary screen shown in FIG. 3C. Accordingly, the screen 100 includes a selectable option of, ALARM TYPE AUDIO FILE, and a list of audio files at the user's disposal. In an exemplary embodiment, a user may choose option 102 labeled ALARM TYPE 2 AUDIO FILE. In so doing, the user may choose an audio file having the desired audio characteristics, such as having a desired fixed audible frequency with a fixed time interval between each beep. Alternatively, ALARM TYPE 2 may comprise a song, a melody, a chime, or any other audio format storable as an audio file. The list 100 may further comprise option 104 representing VOICE ALARM WAVE FILE adapted to use an audio file of a voice or oral message as the configured alarm. Accordingly, in choosing option 104, the patient monitor 12 is configured to voice a verbalized alarm stating, for example, "oxygen saturation level is below 80%."

The screen 100 may further include selectable option 106, corresponding to a selection labeled DOWNLOAD AUDIO FILE. Accordingly, selecting this option configures the patient monitor 12 to download audio files from a connected network, computer or electronic device. Further, the screen 100 includes an option 108 denoted PLAY SAMPLE, enabling the user to hear a sample of one of an available audio file. Lastly, screen 100 includes an option 109 denoted BACK, enabling the user to return to a previous screen.

In an exemplary embodiment in which option 102 ALARM TYPE 2 AUDIO FILE has been chosen, the user is sequentially prompted to screen 120 shown in FIG. 3D. The screen 120 is labeled ALARM TYPE 2 SETTINGS. Accordingly, the screen 120 lists selectable options, enabling the clinician to further tailor the chosen alarm 102. For example, screen 120 includes a VOLUME LEVEL setting 124 which overrides the default VOLUME setting 88 for alarm 102. Accordingly, using the keypad 20 the user can enter an alpha numeric key to set the desired volume level. Further, screen 120 includes option 126 which reads PLAYBACK SPEED LEVEL, enabling the user to set the playing speed of the alarm by entering an alphanumeric key in box 127. The screen 120 further includes a TONE option 128, comprising selectable options settings CONTINUOUS and INTERMITTENT modes of the alarm. For example, in the INTERMITTENT mode, the alarm 102 may comprise beep tone trains comprising a series of beeps and silent intervals between consecutive trains. Alternately, a CONTINUOUS mode would configure the alarm 102 to have no silent interval between each beep train.

In another exemplary embodiment, alarm 102 may include an audio file of a song or melody. Accordingly, configurable setting 130, labeled PLAY PORTION NUMBER, enables the user to select a portion of the song or the melody when the alarm is sounded. As such, the portion number of the song or melody can be entered as an alpha numeric key in box 131, which configures the patient monitor 12 to play the portion of the song corresponding to the alpha numeric key entered.

Referring again to the exemplary embodiment in which the alarm 102 comprises a series of beeps, screen 120 may further include selectable option 134 denoted as MODULATE ALARM BY with corresponding audio file options: MELODY 1, MELODY 2, MELODY 3 . . . etc. Accordingly option 134 modulates the beeps of alarm 102 with a certain melody chosen by the user. Thus, for example, in a children's hospital it may be preferable to have alarm 102 be modulated by a children's song or nursery rhyme, such that every other note of the song is accentuated by a beep of the alarm 102. Accordingly, embodiment 102 comprises a PLAY SAMPLE option 108 permitting the clinician to listen to any configuration chosen from list 120.

Upon choosing the ALARM/AUDIO FILE option 84 in screen 80, the user may further be prompted to an exemplary screen 150 shown in FIG. 3E. In an exemplary embodiment, the user is prompted to screen 150 after completing screen 120. Screen 150, labeled TIME SETTINGS, comprises alarm duration settings, alarm activation setting, etc. For example, a user option 152 labeled ALARMS SOUNDS EVERY, enables the user to choose the time interval between each sounding of alarm 102 by entering an alpha numeric key in box 153. This option is analogous to the INTERMITTENT mode of option 128; however option 152 is more flexible in that it enables variable intermittency settings of the alarm 102.

Further, screen 150 includes user option 154 denoted ACTIVATE ALARM BETWEEN. Hence, a user can set a time of day or period of time during which the alarm may be active. For example, during hours in which a patient may rest or sleep it may be desirable to silence the alarm. Additionally, screen 150 includes an option 156 labeled VARY ALARM OVER TIME. Accordingly, in an exemplary embodiment the user can choose the alarm to become louder and/or faster over time. Further, the screen 150 includes user option 158 labeled CHANGE AUDIO FILES EVERY, which according to the present technique configures an alarm to switch between different AUDIO FILES having different tones and/or melodies during the course of the monitoring period.

Figure 3F:
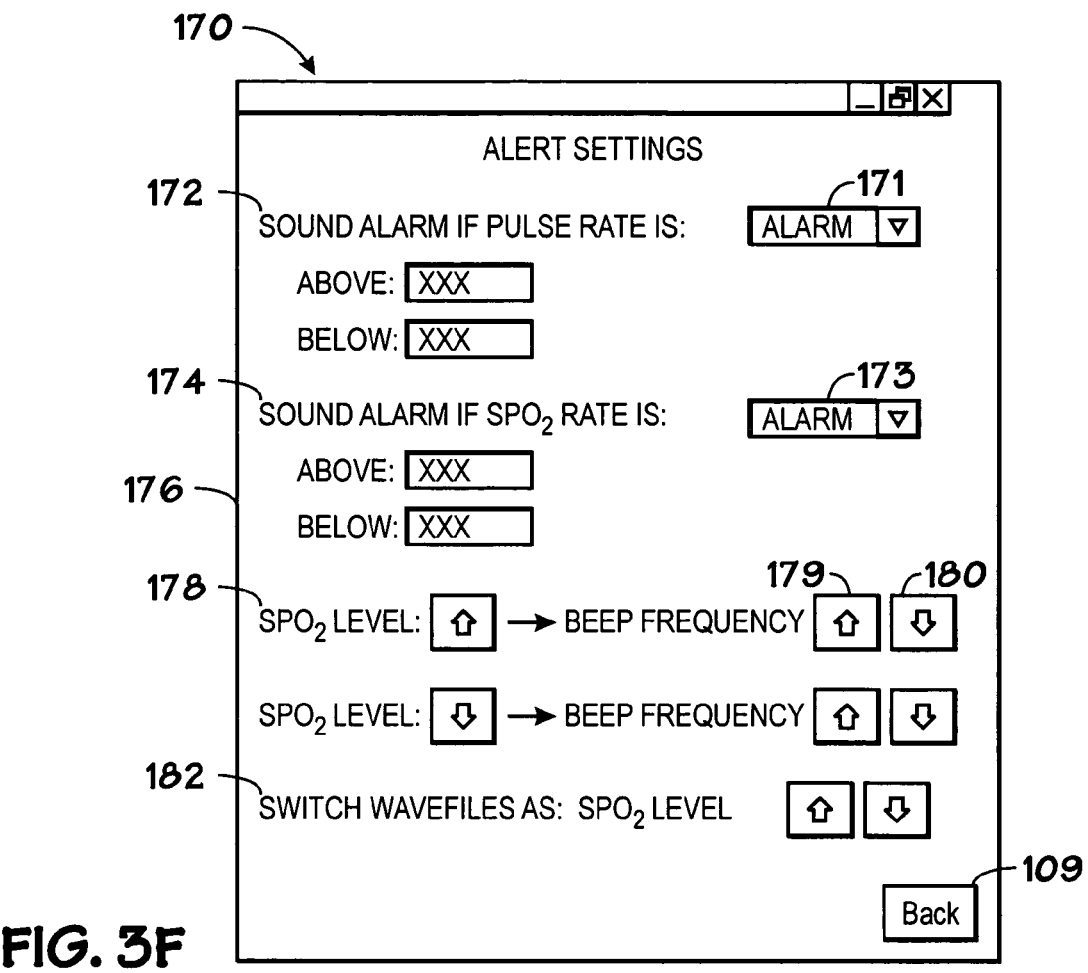

Referring again to FIG. 3A, in an exemplary embodiment that assumes user selection of the ALERT option 86 from menu 80, a clinician is prompted to screen 170 shown in FIG. 3F. The screen 170 is denoted by title, ALERT SETTINGS. Accordingly, the menu 170 comprises audio file alarm and beep settings configured to alert the clinician about occurring changes of physiologically monitored parameters. As such, a clinician may become aware of changes taking place in physiologically monitored parameters without having to visually inspect the monitor. Thus, the configurable alert settings are advantageous, for example, during treatment of the patient the clinician can multi-task and be attentive to the monitoring of physiological parameters, acquired during pulse oximetry.

Accordingly, screen 170 comprises user option 172 labeled SOUND ALARM IF PULSE RATE IS which prompts the user to enter an upper or lower threshold value for the pulse rate. Thus, in an exemplary embodiment, a pulse rate rising above the user entered threshold sounds an alarm generated by a designated audio file that alerts the clinician on the status of the pulse rate. Block 171 includes a pull down menu for choosing an audio file associated with the pulse. Similarly, user option 174 labeled SOUND ALARM IF $SpO_2$ LEVEL IS prompts the user to enter an upper or lower threshold value for oxygen saturation. Accordingly, upon reaching the user entered oxygen saturation threshold an alarm generated by a designated audio file alerts the clinician on the status of the oxygen saturation. Block 173 includes a pull down menu for choosing an audio file associated with the $SpO_2$ level. Thus, by utilizing pull down menus 171 and 173 the user may configure the patient monitor 12 to sound similar or different audio files for monitoring the pulse rate and $SpO_2$ levels. Further, the pull down menus 171 and 173 may support features, such as sounding an audio file whenever a loss of pulse is detected or whenever the sensor 10 is disconnected from the patient monitor or is not properly attached to a patient's body.

Further, screen 170 may include audio file beep settings corresponding to changes in $SpO_2$ levels. User option 178 activates a change in frequency of the alarm beep tones upon detecting changes in the level of oxygen saturation. For example, choosing boxes 179 and/or 180 respectively configure the alert of the patient monitor to increase or decrease the frequency of each beep of the audio file, corresponding to an increase in oxygen saturation. Accordingly, a linear or non-linear function may map the changes of oxygen saturation onto changes in each beep's frequency. Alternatively, the pitch of the alarm beep may change according to the changes in $SPO_2$ levels.

Additionally, in analogy to option 158 of screen 150, screen 170 further comprises an alert setting 182 which enables the user to configure the pulse oximetry system 12 to change audio file alarms in correspondence to changes in levels of oxygen saturation. In an exemplary embodiment, upon detecting a change in oxygen saturation, the pulse oximetry system 12 may sound an audio file randomly selected from a collection of audio files stored in the system's memory.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A pulse oximetry system, comprising:
    a pulse oximetry monitor, comprising:
        a memory;
        a display;
        two or more audio profiles stored in the memory, wherein one of the audio profiles is a default audio profile and the remaining audio profiles each correspond to a different model of pulse oximeter monitor;
        a signal processor configured to:
            cause the display to display a listing of the respective two or more audio profiles;
            receive an indication of a selected audio profile from the listing, wherein the selected audio profile is not the default audio profile;
            generate an audio signal using the selected audio profile in response to a set of physiologic data, wherein the audio signal corresponds to a corresponding audio signal associated with the different model of pulse oximetry monitor; and
        a speaker configured to receive the audio signal from the signal processor.

2. The system, as set forth by claim 1, wherein each of the two or more the audio profiles comprises a plurality of digital audio files.

3. The system, as set forth by claim 2, comprising one or more external memory devices adapted to store digital audio files.

4. The system, as set forth by claim 1, comprising a pulse oximetry sensor configured to transmit data to at least one of the memory or the signal processor.

5. The system, as set forth by claim 1, comprising programmable source code stored in the memory and executed by the signal processor, wherein the programmable source code, when executed by the processor, generates the audio signal.

6. A method for monitoring physiological parameters, comprising the acts of:
    displaying a plurality of audio profile selections, each corresponding to a different model of medical monitor;
    receiving an input indicating a selected audio profile to be used in place of a default audio profile;
    obtaining physiological data; and
    generating an audible signal using the selected audio profile in response to the physiological data, wherein the audible signal emulates an audio response to the physiological data by the model of medical monitor corresponding to the selected audio profile.

7. The method, as set forth by claim 6, wherein obtaining physiological data comprises obtaining pulse oximetry data.

8. The method, as set forth by claim 6, comprising the act of:
   administering a medical treatment based on the audible signal.

9. The method, as set forth by claim 6, comprising the act of:
   utilizing one or both of an internal and an external speaker to play the audible signal.

10. A non-transitory machine readable medium encoding processor-executable code, the encoded code comprising:
    code which, when executed by a processor, causes the display of a plurality of audio profile selections, each corresponding to a different model of medical monitor;
    code which, when executed by a processor, causes the receipt of an input indicating a selected audio profile to be played in place of a default audio profile;
    code which, when executed by a processor, causes the generation of an audible signal using the selected audio profile in response to a set of physiological data.

11. The non-transitory machine readable medium, as set forth by claim 10, wherein the set of physiological data comprises pulse oximetry data.

12. The non-transitory machine readable medium, as set forth by claim 10, comprising code for configuring one or more parameters of the selected audio profile.

13. The non-transitory machine readable medium, as set forth by claim 10, comprising code for downloading the plurality of audio profile selections via a network connection.

14. A method for configuring an alarm, comprising the acts of:
    displaying a plurality of audio profiles having one or more associated audio signals, wherein at least one of the plurality of audio profiles corresponds to a different model of medical monitoring system;
    receiving an input indicating a selection of an audio profile from the plurality of audio profiles to be played on a medical monitoring system, wherein the selected audio profile is not a default audio profile associated with the medical monitoring system; and
    configuring the medical monitoring system to play one of the audio signals from the one or more audio signals of the selected audio profile based on monitored values of one or more measured physiological characteristics.

15. The method, as set forth by claim 14, wherein configuring the medical monitoring system to play the selected audio profile comprises configuring one or more playback characteristics of the selected audio profile.

16. The method, as set forth by claim 15, wherein the one or more playback characteristics comprise speed, frequency, volume, pitch, tone, or timing of an audible signal derived from the selected audio profile.

17. The method, as set forth by claim 14, wherein configuring the medical monitoring system comprises configuring a different audio file to be played for different respective oxygen saturation levels.

18. The method, as set forth by claim 14, comprising utilizing linear or non-linear functions configured to map states of the physiological parameters on to different audible signals derived from the selected audio profile.

19. A method of configuring a patient monitoring system, comprising: storing two or more digital audio file profiles on one or more memory media of the patient monitoring system, wherein each digital audio file profile comprises one or more audio files, and wherein one of the digital audio file profiles is a default audio profile for the patient monitoring system and wherein at least one of the remaining digital audio file profiles corresponds to an audio profile for a different model of patient monitoring system and;
    programming a signal processor to:
      cause a display of the patient monitoring system to display a listing of the audio profiles corresponding to a different model of patient monitoring system;
      receive an indication of a selected audio profile from the listing;
      generate an audio signal using the selected audio profile in response to a set of physiologic data file instead of the default audio profile, wherein the audio signal corresponds to a corresponding audio signal associated with a different model of patient monitoring system.

20. The method, as set forth by claim 19, wherein the memory media is on the patient monitoring system.

* * * * *